US009580365B2

(12) United States Patent
Sun et al.

(10) Patent No.: US 9,580,365 B2
(45) Date of Patent: Feb. 28, 2017

(54) PROCESS AND CATALYST FOR CONVERSION OF ACETIC ACID TO ISOBUTENE AND PROPYLENE

(71) Applicants: Archer Daniels Midland Company, Decatur, IL (US); Washington State University, Pullman, WA (US)

(72) Inventors: Junming Sun, Pullman, WA (US); Changjun Liu, Pullman, WA (US); Yong Wang, Pullman, WA (US); Kevin Martin, Mt. Zion, IL (US); Padmesh Venkitasubramanian, Forsyth, IL (US)

(73) Assignee: Archer-Daniels-Midland-Company, Decatur, IL (US)

( * ) Notice: Subject to any disclaimer, the term of this patent is extended or adjusted under 35 U.S.C. 154(b) by 48 days.

(21) Appl. No.: 14/683,236

(22) Filed: Apr. 10, 2015

(65) Prior Publication Data
US 2015/0239800 A1 Aug. 27, 2015

Related U.S. Application Data

(63) Continuation of application No. PCT/US2013/062784, filed on Oct. 1, 2013, and a continuation of application No. PCT/US2013/063968, filed on Oct. 9, 2013, and a continuation of application No. PCT/US2013/063644, filed on Oct. 13, 2013.

(60) Provisional application No. 61/720,433, filed on Oct. 31, 2012, provisional application No. 61/737,312, (Continued)

(51) Int. Cl.
C07C 1/00 (2006.01)
C07C 1/20 (2006.01)
C07C 1/207 (2006.01)

(52) U.S. Cl.
CPC ............ *C07C 1/2078* (2013.01); *C07C 1/207* (2013.01); *C07C 2521/06* (2013.01); *C07C 2523/06* (2013.01)

(58) Field of Classification Search
CPC .......................... C07C 1/2078; C07C 2523/06
See application file for complete search history.

(56) References Cited

U.S. PATENT DOCUMENTS

2006/0161035 A1* 7/2006 Kalnes ...................... C07C 1/20
585/639

OTHER PUBLICATIONS

Sun et al., Jun. 2011, Direct conversion of bio-ethanol to isobutene on nanosized ZnxZryOz mixed oxides with balanced acid-base sites, JACS, vol. 133, pp. 11096-11099.*

* cited by examiner

*Primary Examiner* — In Suk Bullock
*Assistant Examiner* — Youngsul Jeong
(74) *Attorney, Agent, or Firm* — William B. Miller

(57) ABSTRACT

A process is disclosed for converting acetic acid to propylene and isobutene as the principal hydrocarbon products made, in the presence of a catalyst and in the further presence of hydrogen. In certain embodiments, a $Zn_xZr_yO_z$ mixed oxide catalyst is used for carrying out a gas phase process, and propylene is produced preferentially to isobutene by using at least a certain amount of hydrogen in the process. In some embodiments, a $Zn_xZr_yO_z$ mixed oxide catalyst made by an incipient wetness impregnation method is used and is indicated to be very stable for carrying out the conversion.

12 Claims, 5 Drawing Sheets

Related U.S. Application Data filed on Dec. 14, 2012, provisional application No. 61/836,190, filed on Jun. 18, 2013.

PROCESS AND CATALYST FOR CONVERSION OF ACETIC ACID TO ISOBUTENE AND PROPYLENE

CROSS-REFERENCE TO RELATED APPLICATIONS

The present application is a continuation of International Application No. PCT/US2013/063644 filed Oct. 7, 2013, now published as WO 2014/204509, which directly claims the benefit of U.S. Provisional Application No. 61/836,190 filed Jun. 18, 2013; the present application is also a continuation of International Application No. PCT/US2013/063968 filed Oct. 9, 2013, now published as WO 2014/092849, which directly claims the benefit of U.S. Provisional Application Ser. No. 61/737,312 filed Dec. 14, 2012; and, the present application is also a continuation of International Application No. PCT/US2013/062784 filed Oct. 1, 2013, now published as WO 2014/070354, which directly claims the benefit of U.S. Provisional Application Ser. No. 61/720,433 filed Oct. 31, 2012.

TECHNICAL FIELD

This application concerns renewable source-derived isobutene and propylene and processes for making isobutene and propylene.

BACKGROUND ART

Isobutene is widely used for the production of a variety of industrially important products, such as butyl rubber for example. Isobutene has been produced commercially to date through the catalytic or steam cracking of fossil feedstocks, and the development of a commercially viable process for the manufacture of isobutene from a renewable source-based feedstock is increasingly important as fossil resources are depleted and/or become more costly to use—especially in consideration of increased demand for isobutene.

In view of this need, a hard-template method had been described in the published literature for synthesizing $Zn_xZr_yO_z$ mixed oxides for the direct and high yield conversion of ethanol (from the fermentation of carbohydrates from renewable source materials, including biomass) to isobutene, wherein ZnO was added to $ZrO_2$ to selectively passivate zirconia's strong Lewis acidic sites and weaken Brönsted acidic sites while simultaneously introducing basicity. The objectives of the hard template method were to suppress ethanol dehydration and acetone polymerization, while enabling a surface basic site-catalyzed ethanol dehydrogenation to acetaldehyde, an acetaldehyde to acetone conversion via aldol-condensation/dehydrogenation, and a Brönsted and Lewis acidic/basic site-catalyzed acetone-to-isobutene reaction pathway.

High isobutene yields were in fact realized, but unfortunately, as later experienced by Mizuno et al. (Mizuno et al., "One—path and Selective Conversion of Ethanol to Propene on Scandium-modified Indium Oxide Catalysts", *Chem. Lett.*, vol. 41, pp. 892-894 (2012)) in their efforts to produce propylene from ethanol, it was found that further improvements in the catalyst's stability were needed.

SUMMARY OF THE INVENTION

In response to this need, we have found that these improvements could be realized without adding modifying metals and without a reduction in the initial high activity (100 percent ethanol conversion) that had been observed in these mixed oxide catalysts. Further, we found that the same improved catalysts were effective for making renewable source-based isobutene from acetic acid as a feedstock, rather than ethanol.

The present invention concerns the still further discovery that the $Zn_xZr_yO_z$ mixed oxide catalysts (whether made by the hard template method or by the method of the '433 application) are also able, in the presence of hydrogen, to produce renewable source-based propylene from acetic acid. Additionally, propylene can be produced as the more favored product from the acetic acid, in comparison to the isobutene product.

Accordingly, in a first aspect, the present invention relates to a process for converting acetic acid to propylene in the presence of a catalyst, and in the further presence of hydrogen. Propylene is itself an important industrial chemical, and the capacity to selectively produce propylene in a certain proportion alongside isobutene through using the same mixed oxide catalyst (by adjusting the amount of hydrogen used and/or by additional adjustments in reaction conditions as further illustrated hereafter) adds substantial value for those skilled in the art.

Thus, in a second aspect, the invention can be understood as relating to a process for converting acetic acid to both of propylene and isobutene as co-products. In particular embodiments, propylene is produced preferentially compared to isobutene. In certain of these embodiments, the relative proportion of propylene and isobutene products is altered by adjusting the amount of hydrogen present.

Since acetic acid can be made by a variety of methods from a number of different starting materials, including through carbonylation of methanol derived from sequestered carbon dioxide, for example, the capability of these mixed oxide catalysts to catalyze the conversion of acetic acid to such valuable products enables a range of options for utilizing renewable resources more efficiently, all as described in greater detail hereafter.

DESCRIPTION OF EMBODIMENTS

Figure 1:
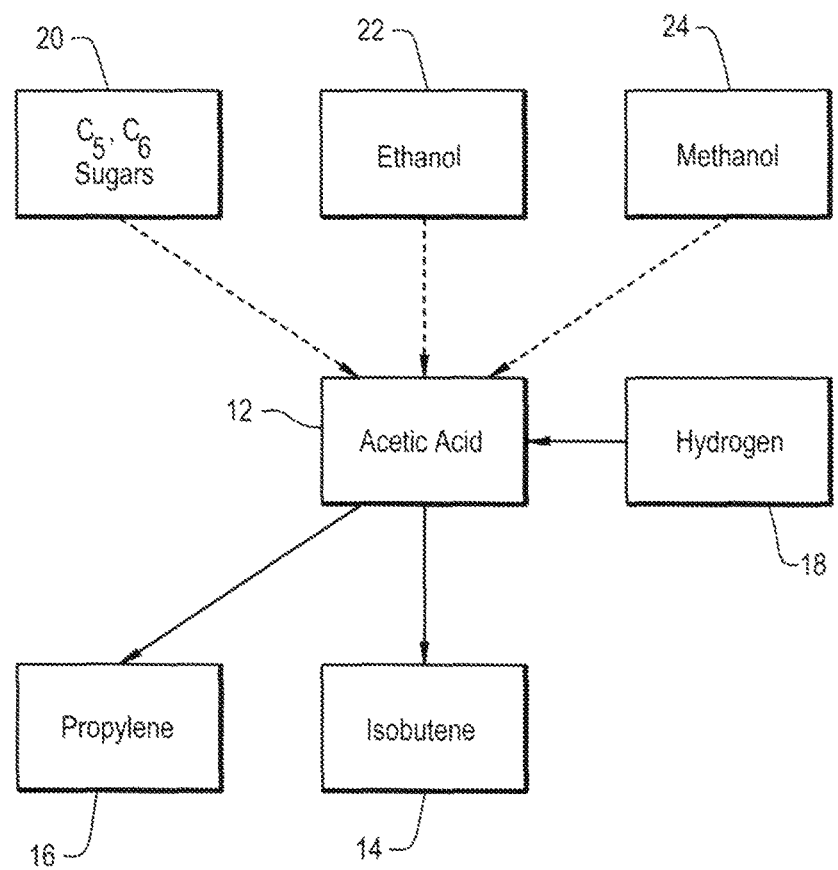
FIG. 1 schematically depicts particular embodiments of a process according to the second aspect, wherein acetic acid is converted to propylene and isobutene in the presence of a catalyst and in the further presence of hydrogen, wherein various options for obtaining the acetic acid are suggested.

Referring now to FIG. 1, a preferred but purely illustrative embodiment 10 of a process of the present invention is schematically illustrated, wherein acetic acid 12 is converted to isobutene 14 and propylene 16 in the presence of a catalyst and further in the presence of hydrogen from a source 18 of such hydrogen. A suitable catalyst is a $Zn_xZr_yO_z$ mixed oxide catalyst.

In one embodiment, the $Zn_xZr_yO_z$ mixed oxide catalyst can be made by a "hard template" or "confined space synthesis" method generally of the character used by Jacobsen et al., "Mesoporous Zeolite Single Crystals", Journal of the American Chemical Society, vol. 122, pp. 7116-7117 (2000), wherein nanozeolites were prepared.

More particularly, the same carbon black (BP 2000, Cabot Corp.) may be used as a hard template for the synthesis of nanosized $Zn_xZr_yO_z$ mixed oxides, rather than nanozeolites as in Jacobsen et al. Prior to use, the BP 2000 template is dried, for example, at 180° C. overnight. Calculated amounts of zirconyl nitrate hydrate (Sigma-Aldrich, greater than 99.8% purity) and $Zn(NO_3)_2.6H_2O$ (Sigma-Aldrich, greater than 99.8% purity) are dissolved in a given amount of water, and sonicated for 15 minutes to produce a clear solution with desired concentrations of Zn and Zr. In one preparation, about 25 grams of the obtained solution are then mixed with 6.0 grams of the preheated BP 2000 to achieve incipient wetness, and the mixture is transferred to a ceramic crucible and calcined at 400 degrees Celsius for 4 hours, followed by ramping the temperature to 550 degrees Celsius (at a ramp rate of 3 degrees Celsius/minute) and holding at 550 degrees Celsius for another 20 hours. Nanosized white powders are obtained, having a mean particle size of less than 10 nanometers.

Alternatively and preferably, the $Zn_xZr_yO_z$ mixed oxide catalysts may be made as described in the '433 application, by a process broadly comprising, in certain embodiments, forming a solution of one or more Zn compounds, combining one or more zirconium-containing solids with the solution of one or more Zn compounds so that the solution wets the zirconium-containing solids to a state of incipient wetness, drying the wetted solids, then calcining the dried solids. In other embodiments, a solution is formed of one or more Zr compounds, the solution is combined with one or more Zn-containing solids so that the solution wets the Zn-containing solids to a state of incipient wetness, the wetted solids are dried and then the dried solids are calcined.

In certain embodiments, the $Zn_xZr_yO_z$ mixed oxide catalysts (whether made by the hard template method or an incipient wetness method according to the '433 application) are characterized by a Zn/Zr ratio (x:y) of from 1:100 to 10:1, preferably from 1:30 to 1:1, especially 1:20 to 1:5, and still more preferably 1:12 to 1:10.

Parenthetically, in the present application where any range of values is given for any aspect or feature of these catalysts or any process described for using these catalysts, the given ranges will be understood as disclosing and describing all subranges of values included within the broader range. Thus, for example, the range of 1:100 to 10:1 will be understood as disclosing and describing not only the specific preferred and more preferred subranges given above, but also every other subrange including a value for x between 1 and 10 and every other subrange including a value for y between 1 and 100.

The catalysts made by the preferred incipient wetness method are consistent in their particle size with the catalysts described in the incorporated journal article, namely, comprising aggregates of less than 10 nm-sized particles with a highly crystalline structure. The Zn oxide component is again highly dispersed on the Zr oxide component.

In certain embodiments, the $Zn_xZr_yO_z$ mixed oxide catalysts are characterized as low sulfur catalysts, containing less than 0.14 percent by weight of sulfur. In the '433 application, the catalysts made by the incipient wetness method were indicated as desirably substantially sulfur-free, preferably including less than 0.01 percent by weight of sulfur and more preferably including less than 0.001 weight percent of sulfur. It was postulated that the reduced sulfur content enabled by the incipient wetness method as compared to the hard template method contributed significantly to the much improved stability observed for the incipient wetness method catalysts of the prior related application for the ethanol to isobutene process.

In the context of the process of the '312 application, namely, in employing a $Zn_xZr_yO_z$ mixed oxide catalyst to convert acetic acid rather than ethanol to isobutene, in at least some embodiments and under certain process conditions some sulfur did appear to be beneficial, though it was again expected that the amount of sulfur would preferably be such that the catalysts are characterized as low sulfur catalysts. Such low sulfur catalysts are most readily made by the incipient wetness method described briefly above and in greater detail in the '433 application.

In principle, provided the zinc and zirconium compounds and solids in these embodiments have a sufficiently low sulfur content in order to produce a low sulfur content when combined according to the preferred incipient wetness method of the '433 application, any combination of zinc and zirconium materials and any solvent can be used that will permit the zinc and zirconium components to mix homogeneously whereby, through incipient wetness impregnation, one of the zinc or zirconium components are well dispersed on a solid of the other component for subsequent drying and conversion to the oxide forms through calcining. As exemplified in the '433 application, low sulfur catalysts can also be made by the incipient wetness method starting with zinc and zirconium compounds that are sulfur-free or substantially sulfur-free, then doping in a desired sulfur content.

The conditions and times for the drying and calcining steps of an incipient wetness preparation will depend, of course, on the particular zinc and zirconium materials and solvent used, but in general terms, the drying step can be accomplished in a temperature range of from 60 degrees Celsius to 200 degrees Celsius over at least 3 hours, while the calcining can take place at a temperature of from 300 degrees Celsius to 1500 degrees Celsius, but more preferably a temperature of from 400 to 600 degrees Celsius is used. The calcination time can be from 10 minutes to 48 hours, with from 2 to 10 hours being preferred.

In still other embodiments, low sulfur catalysts as described herein could be prepared by a hard template method as described in the earlier incorporated publication, except that a suitably very low sulfur content carbon is used for the hard template to realize a low sulfur content in the finished catalyst.

In certain embodiments, the process 10 can be conducted continuously in the gas phase, using a fixed bed reactor or flow bed reactor. The reaction temperature may be in a range from 350 to 700 degrees Celsius, preferably, in a range from 400 to 500 degrees Celsius, and the WHSV can be in a range from $0.01\ hr^{-1}$ to $10\ hr^{-1}$, preferably from $0.05\ hr^{-1}$ to $2\ hr^{-1}$. Acetic acid/water solutions with steam to carbon ratios from 0 to 20, preferably from 2 to 5 can be used to provide acetic acid to the catalyst.

Hydrogen is supplied from a source 18, generally in combination with an inert carrier gas such as nitrogen. As demonstrated by Examples 5 through 8 below, by adjusting the partial pressure of hydrogen in the reactor (all other conditions remaining the same), greater or lesser proportions of propylene relative to isobutene can be produced as desired based on the relative value of these products to the manufacturer at any given time; where no hydrogen is present, isobutene can be produced exclusively, while in the presence of greater amounts of hydrogen propylene can be made preferentially compared to isobutene.

With the particular catalyst and under the particular reaction conditions employed in the referenced Examples 5-8 below, for example, wherein more than 20 percent by volume of the nitrogen (or other inert carrier gas) is displaced with an equivalent volume of hydrogen, propylene begins to be produced (in a process otherwise carried out as described in the '312 application) preferentially compared to isobutene; above roughly an 80:20 mixture of hydrogen to nitrogen by volume, however, additional methane and ethylene are formed, with a reduction in isobutene and with no increase in propylene selectivity. Consequently, for the particular catalyst and under the particular reaction conditions of Examples 5 through 8, if propylene and isobutene were the first and second most desired products from the process, hydrogen would comprise at least 20 percent by volume but not more than 80 percent by volume of a combined hydrogen/nitrogen gas mixture.

The maximum proportion of propylene that can be achieved by adjusting the partial pressure of hydrogen in a reactor can be expected to vary somewhat based on differences in reaction temperature, in the use of different $Zn_xZr_yO_z$ mixed oxide-type catalysts (whether made by the hard template or incipient wetness methods) and other like considerations, but generally it is expected that at least some proportion of isobutene will always be present as a co-product with propylene, even using pure hydrogen—in contrast to the production of isobutene to the exclusion of propylene that is enabled where no hydrogen is present. In any event, it is considered that those skilled in the art will be well able by routine optimization to determine how much hydrogen is needed to produce the desired propylene and isobutene products in an economically advantageous proportion to one another.

As shown schematically in FIG. 1, the acetic acid 12 can be obtained by various methods from a number of starting materials, which in turn permits a number of integrated processes to be considered for providing improved utilization of renewable resources.

For example, acetic acid can be produced from a source of five and six carbon sugars 20 by fermentation. U.S. Pat. No. 6,509,180 and U.S. Pat. No. 8,252,567 seek to improve upon known processes for making ethanol and butanol/hexanol, respectively, by means including the fermentation of five and six carbon sugars into acetic acid. In U.S. Pat. No. 6,509,180, the acetic acid is esterified to form an acetate ester which may then be hydrogenated (using hydrogen from, e.g., steam reforming of natural gas, electrolysis of water, gasification of biomass or partial oxidation of hydrocarbons generally) to ethanol. In U.S. Pat. No. 8,252,567, the ethanol formed in this manner can be used to make butanol and hexanol, by subjecting the ethanol with acetate, acetic acid or mixtures thereof to an acidogenic fermentation using, for example, species of the bacteria *Clostridium* (*Clostridium kluyveri* is mentioned), to produce butyrate, butyric acid, caproate, caproic acid or mixtures thereof. These materials then in turn are acidified to convert butyrate and caproate to butyric acid and caproic acid, the butyric and caproic acids are esterified and then the butyric and caproic acid esters undergo reduction by hydrogenation, hydrogenolysis or reduction by carbon monoxide to provide butanol and ethanol.

As related in these two patents and as well known to those skilled in the fermentation art, the fermentation of five and six carbon sugars to form acetic acid can be accomplished by various organisms. More particularly, homoacetogenic microorganisms are able through fermentation to produce acetic acid with 100% carbon yield; these microorganisms internally convert carbon dioxide to acetate, in contrast to a process for producing ethanol from sugars obtained from biomass wherein carbon dioxide is produced as a byproduct.

Examples of homoacetogens given by U.S. Pat. No. 8,252,567 are microorganisms of the genus *Moorella* and *Clostridium*, especially microorganisms of the species *Moorella thermoaceticum* (described as formerly classified as *Clostridium thermoaceticum*) or *Clostridium formicoaceticum*. U.S. Pat. No. 8,252,567 represents that about one hundred known acetogens in twenty-two genera were known as of 2009, and cross-references Drake, et al., Ann. NY Acad. Sci. 1125: 100-128 (2008) for a review of acetogenic microorganisms.

Other references describing fermentation methods for producing acetic acid from five and six carbon sugars include U.S. Pat. No. 4,935,360; U.S. Pat. No. 8,236,534; U.S. Pat. No. 4,513,084; U.S. Pat. No. 4,371,619 and U.S. Pat. No. 4,506,012; both one-step fermentation processes from the sugars to acetic acid, acetates or both are disclosed, as well as two-step processes involving a first fermentation to lactic acid (by lactobacillus or known methods of homolactic fermentation, preferably) followed by a second fermentation to convert lactic acid to acetic acid, for example, using *Clostridium formicoaceticum*.

Any of the known fermentation methods may, in short, be used to produce acetic acid for conversion to isobutene and propylene in the presence of the mixed oxide catalysts of the present invention and in the further presence of hydrogen, but homoacetogenic fermentation methods are considered preferable in that carbon dioxide is not produced as a byproduct—the carbon dioxide represents a yield loss from the overall process to make isobutene and as a greenhouse gas is undesirable particularly in the context of a process to make a needed product more sustainably from renewable resources.

As well or in the alternative, the acetic acid feedstock 12 can be made from ethanol 22, according to any of several known methods employing oxidative fermentation with acetic acid bacteria of the genus Acetobacter.

As well or in the alternative, the acetic acid feedstock 12 can be made from methanol 24 through combination with carbon monoxide according to the most industrially used route for making acetic acid, for example, in the presence of a catalyst under conditions effective for the carbonylation of methanol. A variety of carbonylation catalysts are known in this regard, see, for example, U.S. Pat. No. 5,672,743; U.S. Pat. No. 5,728,871; U.S. Pat. No. 5,773,642; U.S. Pat. No. 5,883,289; U.S. Pat. No. 5,883,295.

Those skilled in the art will appreciate that making at least a portion of the acetic acid feedstock 12 from methanol 24 would enable other integrated process options to be considered for making isobutene and propylene from a biomass. Thus, syngas may be produced by gasification of a biomass, and methanol then produced from the syngas with additional hydrogen provided, for example, through electrolysis of water. The electrical energy required for the electrolysis may in turn be generated from combustion of additional biomass, through steam from heat energy captured from the methanol synthesis or from combustion of a biomass fraction (lignin, for example), with optional capture and recycle of carbon dioxide from the flue gas to be used in the methanol synthesis. A variety of options for producing methanol from biomass have been presented in the literature, see, for example, US 2007/0254969 A1 by Olah et al; U.S. Pat. No. 6,645,442 and U.S. Pat. No. 6,991,769, both by Kaneko et al; and U.S. Pat. No. 6,340,581 to Gaddy.

Those skilled in the art will appreciate that still other options may be considered for producing acetic acid from biomass or from a biomass fraction, including by catalytic, thermochemical and biological means, and that the limited description of various embodiments provided above should by no means be construed as limiting of the ways in which the acetic acid feedstock 12 may be made using renewable resources inclusive fundamentally of biomass, carbon monoxide and carbon dioxide gases. For example, as is known, the required acetic acid may be made at least in some part by anaerobic fermentation using carbon monoxide and carbon dioxide gases themselves for a carbon source.

The present invention is further illustrated by the following examples:

Example 1

Not of the Invention

Commercial zirconium hydroxide was dried at 120 degrees Celsius for more than 5 hours. A calculated amount of $Zn(NO_3)_2$ (from Sigma-Aldrich, more than 99.8 percent purity) was dissolved in water, forming a clear solution. The dried zirconium hydroxide (which was also from Sigma-Aldrich, more than 99.8 percent purity) was then mixed with the solution by incipient wetness, in order to form wet powders impregnated with Zn. The wetted powder was then dried at 80 degrees Celsius for 4 hours, followed by calcination at 550 degrees Celsius for 3 hours, to obtain a $Zn_1Zr_8O_z$ catalyst by the incipient wetness impregnation method of the '433 application.

The catalyst thus prepared was then placed in a fixed-bed stainless steel reactor having an inside diameter of 5 millimeters, with 100 mg of the catalyst being packed between quartz wool beds. A thermocouple was placed in the middle of the catalyst bed to monitor the reaction temperature. Before beginning the reaction, the catalyst bed was pretreated by flowing 50 ml/minute of nitrogen at 450 degrees Celsius through the catalyst over a half hour. A 25 weight percent solution of acetic acid in water was then introduced into an evaporator at 180 degrees Celsius by means of a syringe pump, and the vaporized steam/acetic acid was carried into the reactor by a flowing nitrogen carrier gas at an acetic acid concentration in the gas phase of 1.36 weight percent and a WHSV of 0.1 grams of acetic acid per gram of catalyst per hour. No hydrogen was input to the reactor. Meanwhile, the product line was heated to in excess of 150 degrees Celsius before a cold trap, to avoid condensing the liquid products in the product line. A reaction temperature of 415 degrees Celsius was employed.

A Shimadzu 2400 gas chromatograph equipped with an auto sampling valve, HP-Plot Q column (30 m, 0.53 mm, 40 μm) and flame ionization detector was connected to the line between the reactor outlet and cold trap to collect and analyze the products in the effluent gas. After the cold trap, an online micro-GC (MicroGC 3000A equipped with molecular sieves 5A, plot U columns and thermal conductivity detectors) was used to analyze the product gases specifically, using nitrogen as a reference gas.

Figure 2:
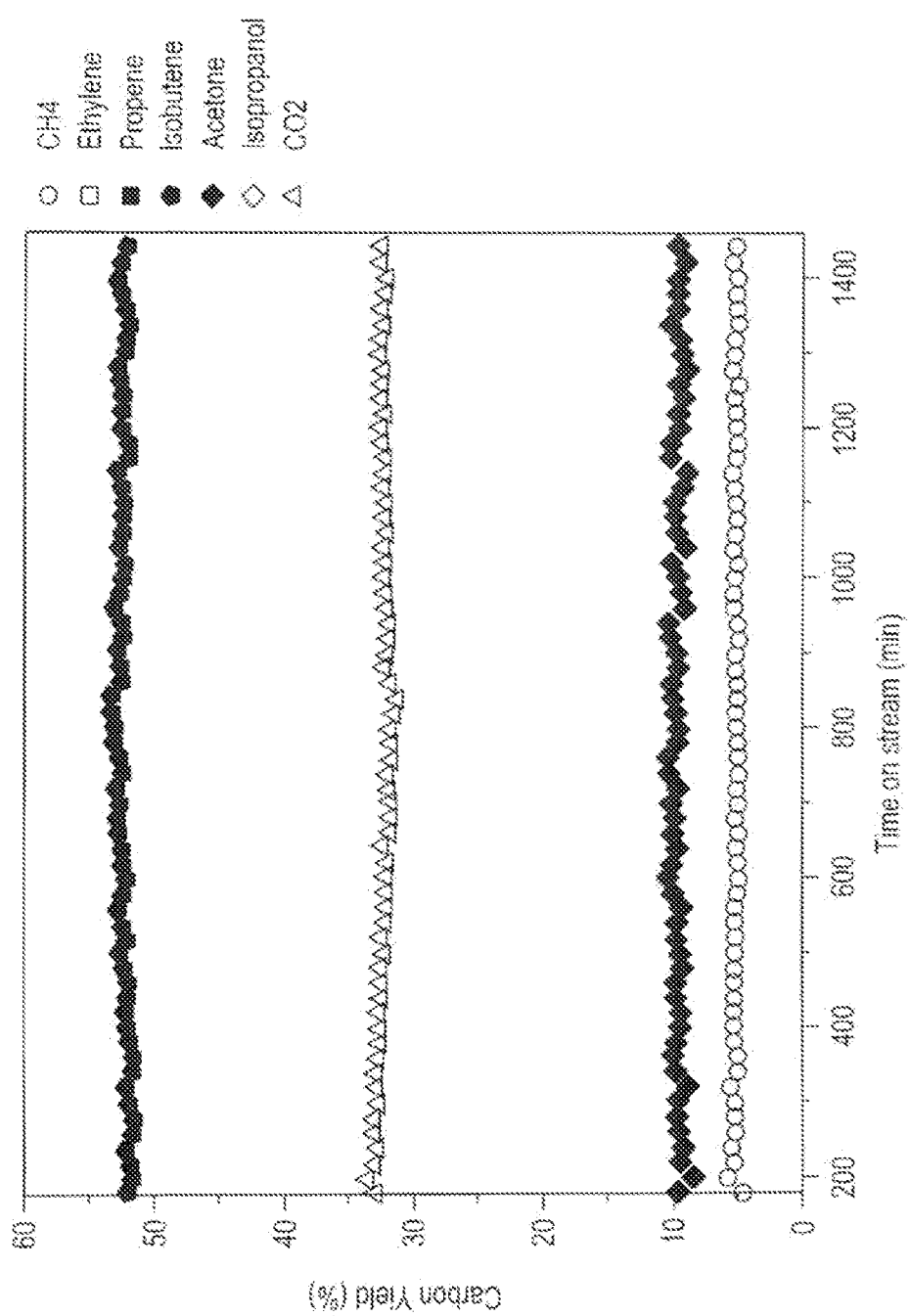
FIG. 2 shows the yields of products in a process according to the '312 application over time, carried out as described in Example 1 (Not of the Invention) below.

FIG. 2 shows the results of a one-pass durability test of the $Zn_1Zr_8O_z$ catalyst prepared by the incipient wetness impregnation method. A consistent product of about 5 percent by weight of methane, about 10 percent by weight of acetone, about 33 percent by weight of carbon dioxide and more than about 50 percent by weight of isobutene was obtained, with, however, no propylene being evident. The catalyst showed very high stability over the full duration of the run, with no signs of observable deactivation after more than 1400 minutes of time-on-stream operation.

Examples 2 and 3

Figure 3:
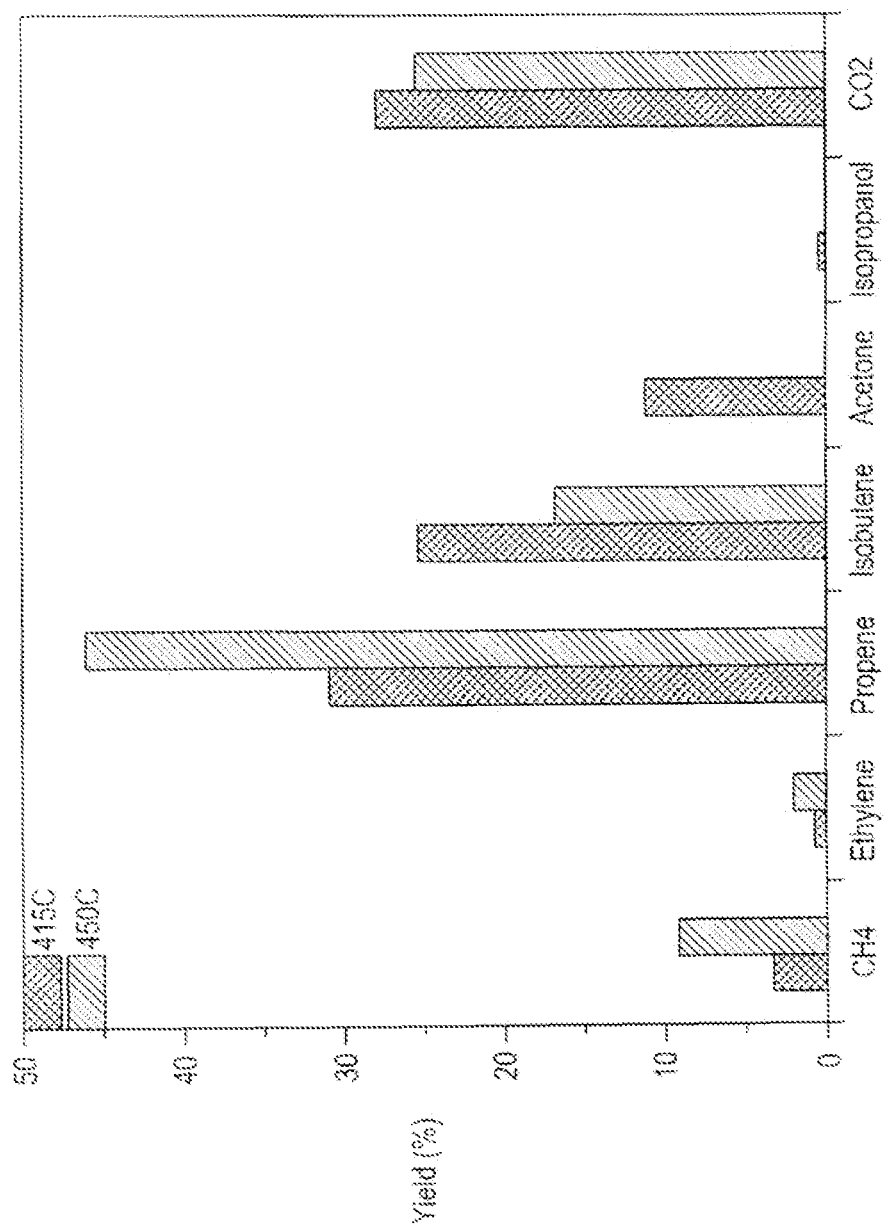
FIG. 3 shows the effect of added hydrogen on the product distribution in the conversion of acetic acid to isobutene in a process otherwise carried out as in the '312 application (and as further described in Examples 2 and 3 below), while employing an improved stability mixed oxide catalyst as described in the '433 application in the presence of the added hydrogen.

The same $Zn_1Zr_8O_z$ catalyst employed in Example 1 was used in generally the same manner, using the same apparatus but at two different reaction temperatures (namely, 415 degrees Celsius (Example 2) and 450 degrees Celsius (Example 3)), and except that a 50/50 volumetric mixture of hydrogen and nitrogen was used for each of Examples 2 and 3 rather than just using the inert nitrogen carrier gas. As shown in FIG. 3, the use of hydrogen resulted in a substantial amount of propylene being formed alongside isobutene, and in fact more propylene was produced than isobutene for each example.

Example 4

Figure 4:
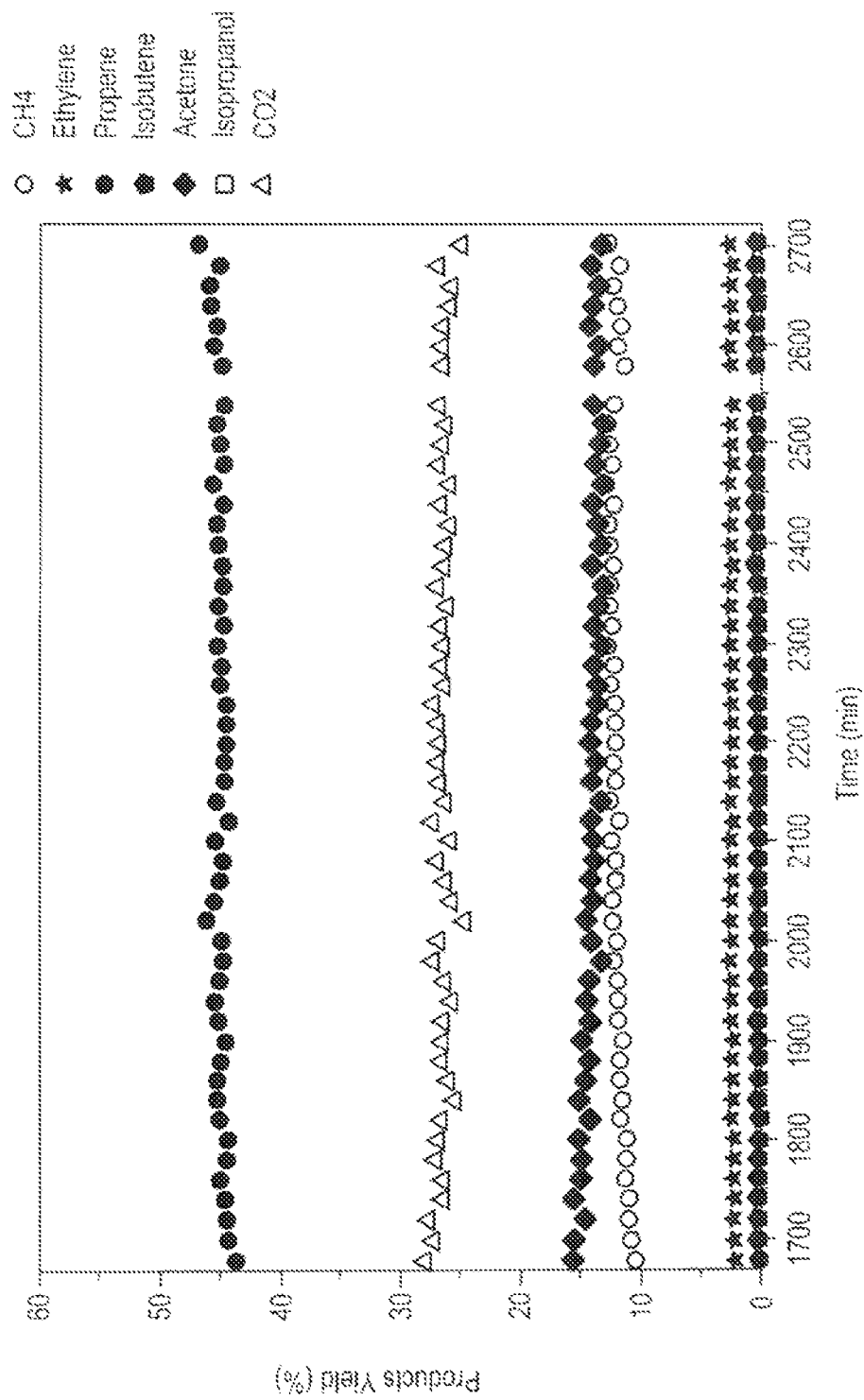
FIG. 4 shows the yields of the various products found in a process of the present invention over time, as described further in Example 5 below.

FIG. 4 shows the results over time in a one-pass durability test of the same $Zn_1Zr_8O_z$ catalyst as used in previous examples, at a reaction temperature of 450 degrees Celsius and using the 50/50 $H_2/N_2$ mixture. After 15 hours on stream, little to no deactivation was observed, indicating the stability seen in Example 1 (Not of the Invention) in converting acetic acid to isobutene was not compromised in producing propylene from acetic acid with the catalyst and with hydrogen addition.

Examples 5 Through 8

Figure 5:
FIG. 5 shows how the product distribution is altered by using different partial pressures of hydrogen in Examples 5 through 8, in converting acetic acid to products including isobutene and propylene over an improved stability mixed oxide catalyst as described in the '433 application.

FIG. 5 displays the varying product distributions realized using a $Zn_1Zr_{10}O_z$ mixed oxide catalyst prepared in the same manner as in Example 1 (Not of the Invention) except in relation to the ratio of Zn to Zr, and run in the manner, using the apparatus and reaction conditions of Example 4 but also varying the amount of hydrogen used in combination with nitrogen. More particularly, mixtures of hydrogen and nitrogen were used that employed 20 volumetric percent, 50 percent, 80 percent and 100 percent of hydrogen, with the balance if any being nitrogen. As previously noted, propylene and isobutene were produced in a roughly 50/50 proportion to one another with the 20/80 mixture of hydrogen and nitrogen, while no greater proportion of propylene was realized relative to isobutene under the conditions tested and with the indicated catalyst above a hydrogen content of about 80 percent.

The invention claimed is:

1. A process for converting acetic acid to propylene and isobutene comprising: reacting hydrogen with acetic acid in the presence of a $Zn_xZr_yO_z$ mixed oxide catalyst in a reactor to form propylene and isobutene, in which the ratio of x:y is from 1:100 to 10:1 and z is a stoichiometric coefficient for the $Zn_xZr_yO_z$ mixed oxide catalyst.

2. A process according to claim 1, wherein propylene is produced preferentially to isobutene.

3. A process according to claim 1 or claim 2, wherein the $Zn_xZr_yO_z$ mixed oxide catalyst contains less than 0.14 percent by weight of sulfur.

4. A process according to claim 3, wherein the $Zn_xZr_yO_z$ mixed oxide catalyst contains less than 0.01 percent by weight of sulfur.

5. A process according to claim 4, wherein the $Zn_xZr_yO_z$ mixed oxide catalyst contains less than 0.001 percent by weight of sulfur.

6. A process according to claim 1, wherein x:y is from 1:30 to 1:1.

7. A process according to claim 6, wherein x:y is from 1:20 to 1:5.

8. A process according to claim 7, wherein x:y is from 1:12 to 1:10.

9. A process according to claim 2, wherein the hydrogen is supplied to the reactor in combination with inert carrier gas.

10. A process according to claim 9, wherein the hydrogen comprises at least 20 percent by volume of a hydrogen and inert carrier gas combination by volume.

11. A process according to claim 9, comprising altering comparative production of propylene and isobutene by adjusting the amount of hydrogen in the hydrogen and inert carrier gas combination.

12. A process according to claim 1, wherein the process is carried out at a temperature in the range of from about 350 to about 700 degrees Celsius and a weight hourly space velocity (WHSV) in the range of from about 0.01 and 10 $hr^{-1}$.

* * * * *